US00PP11807P2

(12) United States Plant Patent
Lyrene

(10) Patent No.: US PP11,807 P2
(45) Date of Patent: Mar. 13, 2001

(54) BLUEBERRY PLANT NAMED 'JEWEL'

(76) Inventor: Paul M. Lyrene, 2211 NW. 58 Ter., Gainesville, FL (US) 32605

( * ) Notice: Subject to any disclaimer, the term of this patent is extended or adjusted under 35 U.S.C. 154(b) by 0 days.

(21) Appl. No.: 09/175,101

(22) Filed: Oct. 19, 1998

(51) Int. Cl.[7] ..... A01H 5/00
(52) U.S. Cl. ..... Plt./157
(58) Field of Search ..... Plt./157

(56) References Cited

U.S. PATENT DOCUMENTS

P.P. 11,033 * 8/1999 Lyrene ..... Plt./157

* cited by examiner

*Primary Examiner*—Bruce R. Campell
*Assistant Examiner*—Wendy Anne Baker

(57) ABSTRACT

A new and distinct low-chill tetraploid highbush blueberry (Vacinnium) variety of complex ancestry, based largely on *V. corymbosum* L with some genes from *V. darrowi* Camp. Its novelty consists of the following unique combination of features:

1. Produces a bush that is upright, but somewhat spreading.
2. Has a medium level of resistance to cane canker (*Botryosphaeria corticis*), stem blight (*Botryosphaeria dothidia*), and root rot (*Phytophthora cinnamomi*).
3. Flowers very early in north central Florida (Gainesville). Date of full bloom in Gainesville averages about February 10, seven days before 'Sharpblue' (an unpatented variety that is widely grown in Florida).
4. Produces numerous flower buds and flowers heavily and synchronously in areas that receive 250 hours or more of temperatures below 45° F. per winter.
5. Ripens 5–7 days earlier than 'Sharpblue'. First commercial harvest averages April 15 in Gainesville, Fla., and peak harvest is about April 25.
6. Produces fruit that are large, firm, have a good picking scar, with tart to sweet flavor and good texture.
7. Can be propagated asexually by softwood cuttings.

3 Drawing Sheets

ORIGIN OF THE VARIETY

'Jewel' was selected as a seedling from a cross-made in Gainesville in 1988. The parents were advanced-generation selections from a recurrent selection program in which the large fruit size, high fruit quality, and short flowering-to-ripening interval of northern highbush cultivars from Michigan and New Jersey were being combined with the low chill requirement, summer heat tolerance, and other southern adaptation features of the native Florida species, *Vaccinium darrowi*. 'Jewel' was selected as a seedling in a high-density nursery in May 1990 and as a spaced plant in the second-evaluation plots in May 1992. The principal selection criteria were large fruit, high fruit quality, early ripening, and strong, leafy bush. Cuttings were taken in the summer of 1992 to establish an 8-plant plot at the University of Florida Horticultural Unit in Gainesville. These ramets were planted in the field in January 1994 and were observed annually during the flowering and fruiting seasons from 1995 through 1998. A 20-plant plot of 'Jewel' was established at Windsor in north-central Florida in January 1997 and was observed during the fruiting seasons of 1997 and 1998. Twenty plants of 'Jewel' were grown in pots of peat in a greenhouse in Gainesville and assessed for the ability to set fruit with self-pollination. 'Jewel' was selected after comparison with many other test selections because of its low chilling requirement, heavy flowering, and high fruit quality.

ASEXUAL PROPAGATION OF THE VARIETY

'Jewel' has been propagated by softwood cuttings on numerous occasions in Gainesville, Fla. (Alachua County).

In every case, all resulting plants have displayed the characteristics of the variety.

BRIEF DESCRIPTION OF THE FIGURES OF THE DRAWING

The first drawing shows a 4-year-old plant of 'Jewel' revealing the upper and lower surfaces of the leaves and the clusters of ripening fruit.

The second drawing shows, in larger scale, clusters of opened and unopened flowers of 'Jewel' indicating the color of the calyx and corolla, the shape of the corolla tubes, and the clustering habit of the flowers in the inflorescence.

The third drawing shows, in large scale, the ripe fruit of 'Jewel', indicating the color and shape of the berry and the shape of the calyx lobes.

DESCRIPTION OF THE VARIETY

The following is a detailed botanical description of 'Jewel', its flowers, fruit and foliage, based on observation of specimens grown in the field in Gainesville, Fla. Color descriptions, except those given in common terms, use terminology from "The Pantone Book of Color" by Leatrice Eiseman and Lawrence Herbert; Harry N. Abrams, Inc. Publishers, New York. While the coloration shown in the photographic illustrations provided is as close as is reasonably possible to attain in an illustration of this character, the color designations provided in the specification should be considered to be the closest possible representation of the coloration of the instant plant.

Bush: Bush size of 4-year old plants grown in medium quality blueberry soil, with irrigation, pine-bark mulch, and annual summer pruning:

*Plant height.*—100 cm.

*Canopy diameter.*—105 cm.

*Vigor.*—Medium.

*Growth habit.*—Semi-upright, somewhat spreading.

*Flower bud density (number per unit length of stem).*—Very high.

*Cold hardiness.*—Except for the flower and the fruit, some of which have been killed in some years in Gainesville, by freezes in February and March, 'Jewel' has not suffered freeze damage to the bush in Gainesville. Dormant plants have withstood temperatures of 18° F. without damage.

*Chilling requirement.*—Based on the time and completeness of vegetative and flower bud break in Sebring, Fla., 'Jewel' appears to have a chilling requirement of about 250 hours below 45° F. after the plants have become winter dormant.

*Productivity.*—Four-year-old plants on medium-good soil in Gainesville have averaged 3 to 4 pounds of fruit per plant per year.

*Suckering tendency.*—After 4 years in the field, plants have 6 to 10 major trunks.

*Color of 2-year-old wood.*—"Pelican", Pantone 14-6305.

*Color of trunks 4 years old and older.*—"Champagne Beige" Pantone 14-012.

Twigs:

*Color of previous summer twigs observed January 30.*—"Moth" Pantone 13-0611.

*Internode length.*—1.2 cm on strong upright shoots.

Leaves:

*Leaf length excluding petiole.*—60 mm.

*Leaf width.*—35 mm.

*Shape.*—Obovate.

*Margin.*—Entire.

*Color of upper surface.*—"Four leaf clover" Pantone 18-0420.

*Color of lower surface.*—"Sage" Pantone 16-0421.

*Pubescence, upper surface.*—Numerous short, white hairs on midribs and main veins.

*Pubescence, lower surface.*—Essentially glabrous.

*Pubescence, leaf margins.*—Essentially glabrous.

*Synchrony of leafing and flowering.*—New leaves begin to form at the time of or shortly after flowering.

Flowers:

*Length, pedicel attachment point to the corolla tip.*—11.0 mm.

*Diameter of corolla tube at widest point.*—8.0 mm.

*Corolla aperture diameter.*—3.2 mm.

*Corolla color at anthesis.*—"Pearl" Pantone 12-1304.

*Flower fragrance.*—None.

*Pollen abundance.*—High.

*Pollen staining with acetocarmine dye.*—Excellent, near 100%. This indicates that nearly all of the pollen grains are well developed and starch filled. Aborted pollen grains will not stain with the procedure used. Because southern highbush blueberries are derived from interspecific hybrids, many clones have reduced pollen fertility. This reduced fertility is indicated by lower percentage of stainable pollen grains. The percentage of stainable pollen varies widely from clone to clone, but is relatively constant within clones. This makes it a useful cultivar descriptor.

*Flowering period.*—Full bloom averages February 10 in Gainesville.

*Flower cluster.*—Medium to open.

*Average number of flowers per cluster.*—5–6. Stamens and pistil are typical for highbush blueberry.

*Self-compatibility.*—Partially self-compatible but must be cross-pollinated for full fruit size and number.

Berry:

*Weight.*—First berries to ripen average 1.7 to 2.5 g.

*Calyx lobes.*—Irregular and not well developed.

*Berry height.*—14 mm.

*Berry width.*—15 mm.

*Diameter of calyx aperture on mature berry.*—6 mm.

*Exterior berry color.*—"Dapple gray" Pantone 16-3907.

*Exterior berry color with surface wax removed.*—"Slate Black", Pantone 19-0814.

*Interior berry flesh color.*—"Frozen Dew" Pantone 13-0513, which is a whitish-green.

*Color of washed, dried seeds.*—"Almond", Pantone 16-1432, a shade of brown.

*Surface wax.*—Medium persistent.

*Pedicel scar.*—Small and dry.

*Berry firmness.*—Medium to high.

*Berry flavor.*—Sweet to tart.

*Berry fragrance.*—None.

*Berry texture.*—Good: thin skins, small seeds, inconspicuous scleroids.

*Resistance to rain cracking.*—Moderately resistant but will crack if wet for over 24 hours.

*Intended market class.*—Fresh fruit.

*Maturity date.*—First pick averages April 15 in Gainesville. Peak harvest about April 25.

Diseases, insects, and mites:

*Cane canker.*—Partially resistant.

*Dieback due to stem blight and root rot.*—Moderately resistant.

*Leaf spots.*—Medium resistant.

*Bud mites.*—Resistant.

Ease of propagation: Roots readily from softwood cuttings.

We claim:

1. A new and distinct southern highbush blueberry variety as illustrated and described, characterized by a low chilling requirement and early season ripening, which produces large fruit of high fresh-market quality.

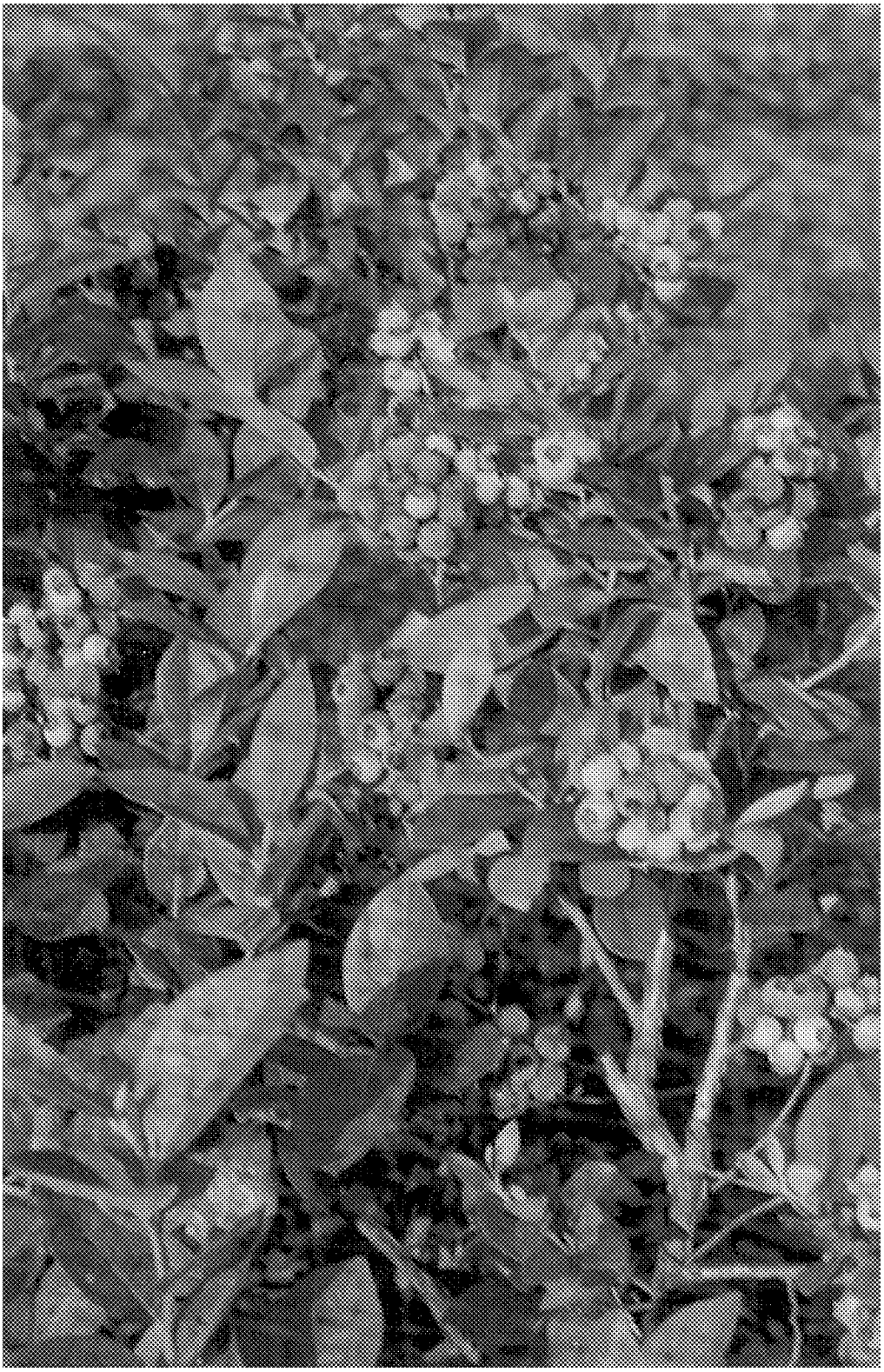

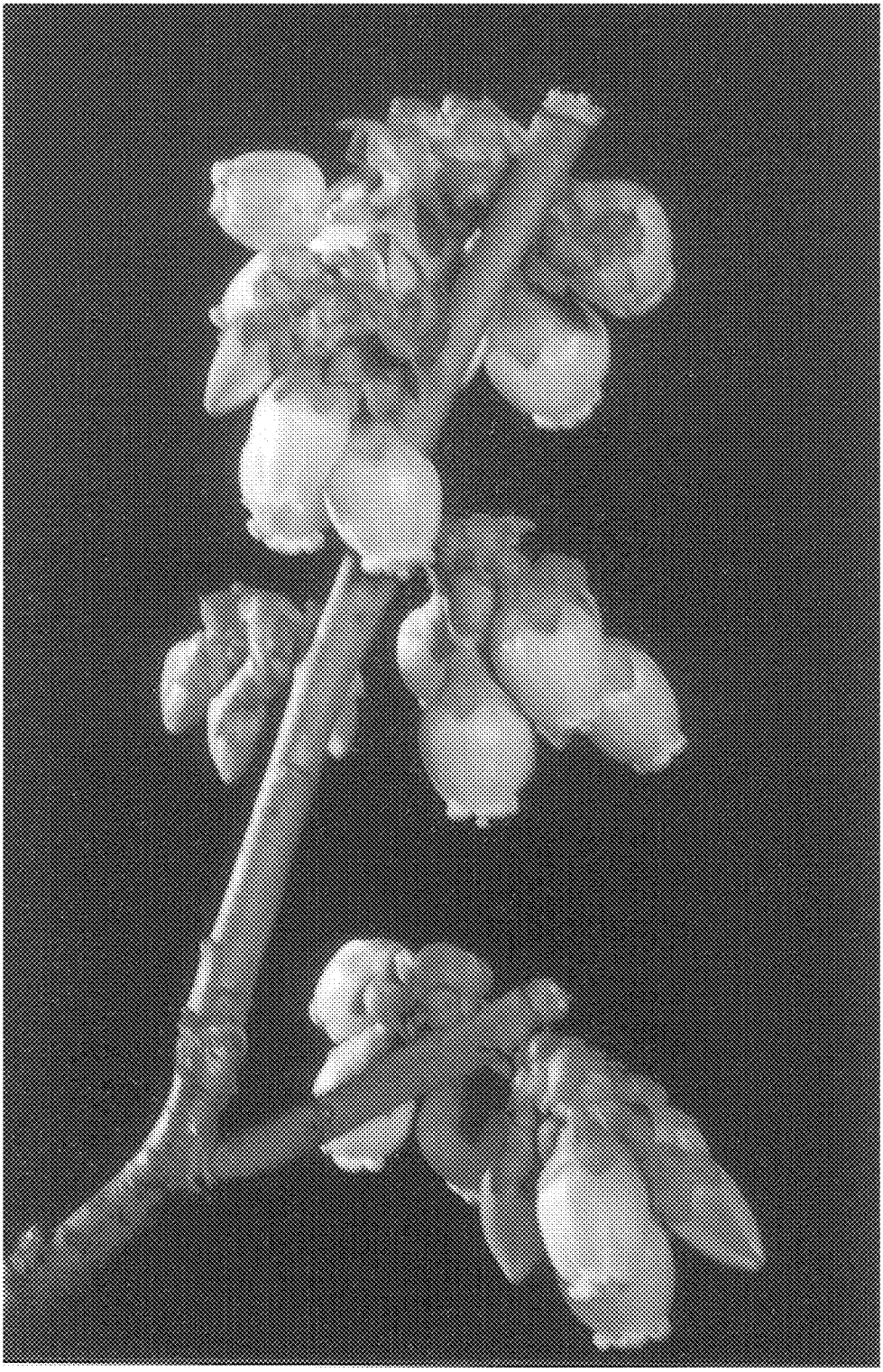

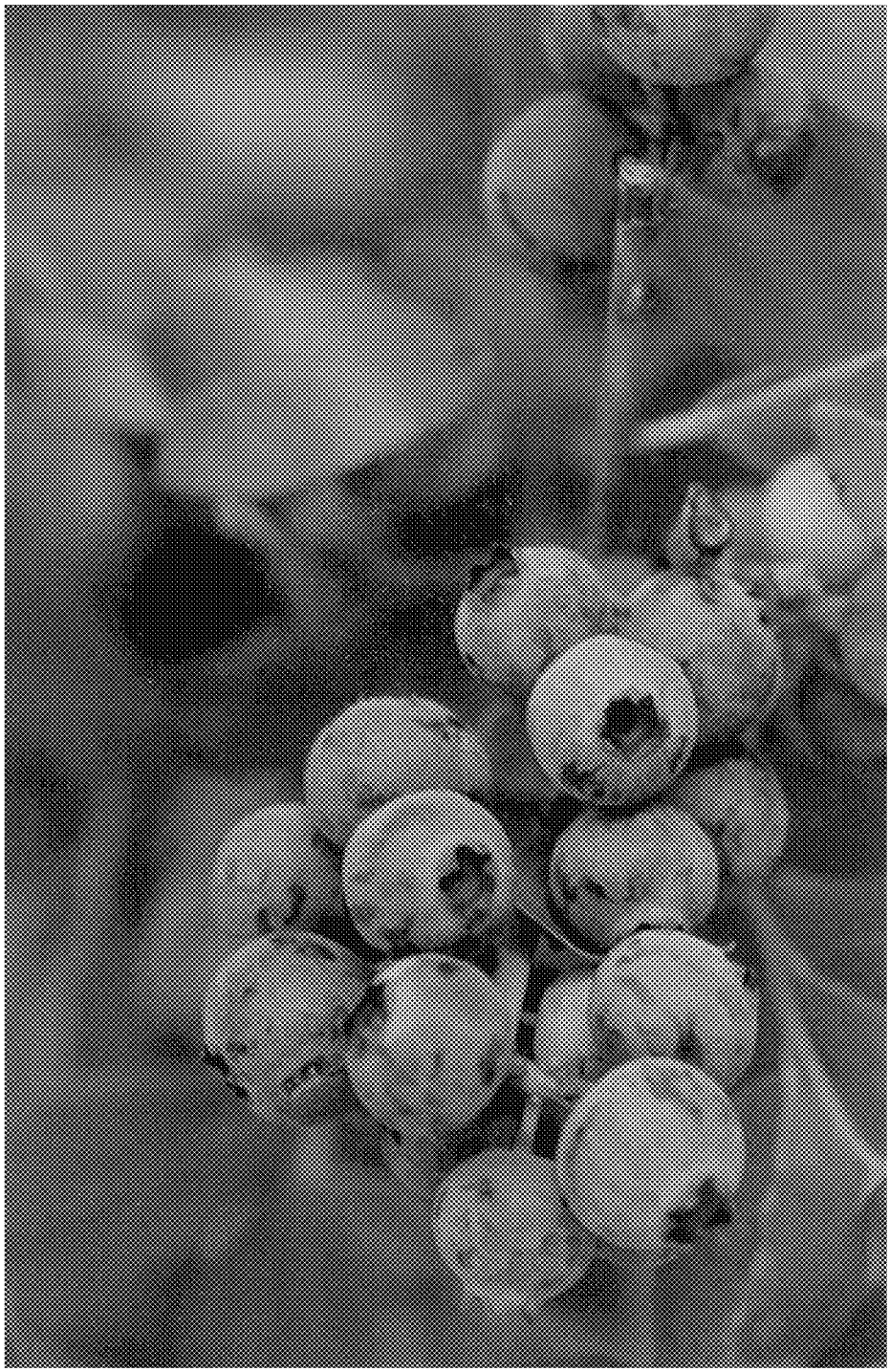

* * * * *